US00PP31765P2

(12) United States Plant Patent
Bisschop et al.

(10) Patent No.: US PP31,765 P2
(45) Date of Patent: May 12, 2020

(54) ***RUDBECKIA* PLANT NAMED 'ET RDB 603'**

(50) Latin Name: ***Rudbeckia hirta* X *Rudbeckia hybrida***
Varietal Denomination: ET RDB 603

(71) Applicants: Elisabeth Bisschop, Boijl (NL); Bart Noordhuis, Boijl (NL)

(72) Inventors: Elisabeth Bisschop, Boijl (NL); Bart Noordhuis, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 0 days.

(21) Appl. No.: 16/501,607

(22) Filed: May 7, 2019

(51) Int. Cl.
*A01H 6/14* (2018.01)
*A01H 5/02* (2018.01)

(52) U.S. Cl.
USPC ..... Plt./474

(58) Field of Classification Search
USPC ..... Plt./474
CPC ..... A01H 6/14; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Rudbeckia* plant named 'ET RDB 603', characterized by its tall and upright to somewhat outwardly spreading and mounded plant habit; relatively small leaves; dense and bushy growth habit; freely flowering habit; large single-type inflorescences with yellow orange and greyed orange bi-colored ray florets positioned above the foliar plane on strong peduncles; and good postproduction and garden performance.

2 Drawing Sheets

Botanical designation: *Rudbeckia hirta* X *Rudbeckia hybrida.*

Cultivar denomination: 'ET RDB 603'.

BACKGROUND OF THE INVENTION

The present invention relates to a new and distinct cultivar of *Rudbeckia* plant, botanically known as *Rudbeckia hirta* X *Rudbeckia hybrida* and hereinafter referred to by the name 'ET RDB 603'.

The new *Rudbeckia* plant is a product of a planned breeding program conducted by the Inventors in Boijl, The Netherlands. The objective of the breeding program is to create new *Rudbeckia* plants with small leaves and large long-lasting and attractive inflorescences on strong peduncles.

The new *Rudbeckia* plant originated from a cross-pollination made by the Inventors in Boijl, The Netherlands in 2015 of a proprietary selection of *Rudbeckia hirta* identified as code designation M3726, not patented, as the female, or seed parent with a proprietary selection of *Rudbeckia hybrida* identified as code designation M1862, not patented, as the male, or pollen, parent. The new *Rudbeckia* plant was discovered and selected by the Inventors as a single flowering plant from within the progeny of the stated cross-pollination in a controlled environment in Boijl, The Netherlands in 2016.

Asexual reproduction of the new *Rudbeckia* by in vitro meristem culture in a controlled greenhouse environment in Boijl, The Netherlands since 2016 has shown that the unique features of this new *Rudbeckia* plant are stable and reproduced true to type in successive generations.

SUMMARY OF THE INVENTION

Plants of the new *Rudbeckia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ET RDB 603'. These characteristics in combination distinguish 'ET RDB 603' as a new and distinct *Rudbeckia* plant:

1. Tall and upright to somewhat outwardly spreading and mounded plant habit.
2. Relatively small leaves.
3. Dense and bushy growth habit.
4. Freely flowering habit.
5. Large single-type inflorescences with yellow orange and greyed orange bi-colored ray florets positioned above the foliar plane on strong peduncles.
6. Good postproduction and garden performance.

Plants of the new *Rudbeckia* differ from plants of the female parent selection in the following characteristics:

1. Plants of the new *Rudbeckia* are taller than plants of the female parent selection.
2. Inflorescences of plants of the new *Rudbeckia* are longer lasting than inflorescences of plants of the female parent selection.

Plants of the new *Rudbeckia* differ from plants of the male parent selection in the following characteristics:

1. Plants of the new *Rudbeckia* are taller and more upright than plants of the male parent selection.
2. Inflorescences of plants of the new *Rudbeckia* are longer lasting than inflorescences of plants of the male parent selection.

Plants of the new *Rudbeckia* can be compared to *Rudbeckia hybrida* 'ET RDB 410', disclosed in U.S. Plant Pat. No. 29,163. Plants of the new *Rudbeckia* differ primarily from plants of 'ET RDB 410' in the following characteristics:

1. Plants of the new *Rudbeckia* are taller than plants of 'ET RDB 410'.
2. Plants of the new *Rudbeckia* have a single row of transitional florets whereas plants of 'ET RDB 410' do not develop transitional florets.
3. Plants of the new *Rudbeckia* and 'ET RDB 410' differ in ray floret color as plants of the new *Rudbeckia* have yellow orange and greyed orange bi-colored ray florets whereas plants of 'ET RDB 410' have yellow and greyed orange bi-colored ray florets.

Plants of the new *Rudbeckia* can also be compared to *Rudbeckia hirta* X *Echinacea purpurea* 'ET-RDB 01', disclosed in U.S. Plant Pat. No. 25,221. Plants of the new *Rudbeckia* differ primarily from plants of 'ET-RDB 01' in the following characteristics:

1. Plants of the new *Rudbeckia* are larger than plants of 'ET-RDB 01'.
2. Plants of the new *Rudbeckia* have larger inflorescences than plants of 'ET-RDB 01'.
3. Plants of the new *Rudbeckia* have a single row of transitional florets whereas plants of 'ET-RDB 01' do not develop transitional florets.
4. Plants of the new *Rudbeckia* and 'ET-RDB 01' differ in ray floret color as plants of the new *Rudbeckia* have yellow orange and greyed orange bi-colored ray florets whereas plants of 'ET-RDB 01' have yellow, orange and red-colored ray florets.

BRIEF DESCRIPTION OF THE PHOTOGRAPHS

The accompanying photographs illustrate the overall appearance of the new *Rudbeckia* showing the colors as true as it is reasonably possible to obtain in colored reproductions of this type. Colors in the photographs may differ slightly from the color values cited in the detailed botanical description which accurately describe the colors of the new *Rudbeckia* plant.

The photograph on the first sheet comprises a side perspective view of a typical flowering plant of 'ET RDB 603' grown in a container.

The photograph on the second sheet is a close-up view of a typical inflorescence of 'ET RDB 603'.

DETAILED BOTANICAL DESCRIPTION

The aforementioned photographs and following observations, measurements and values describe plants grown in 2.5-liter containers during the spring in an outdoor nursery in Boijl, The Netherlands and under cultural conditions typical of commercial *Rudbeckia* production. During the production of the plants, day temperatures averaged 16° C. and night temperatures averaged 10° C. Plants were one year old when the photographs and the detailed description were taken. In the following description, color references are made to The Royal Horticultural Society Colour Chart, 2001 Edition, except where general terms of ordinary dictionary significance are used.

Botanical classification: *Rudbeckia hirta* X *Rudbeckia hybrida* 'ET RDB 603'.

Parentage:

*Female, or seed, parent*.—Proprietary selection of *Rudbeckia hirta* identified as code designation M3726, not patented.

*Male, or pollen, parent*.—Proprietary selection of *Rudbeckia hybrida* identified as code designation M1862, not patented.

Propagation:

*Type*.—By in vitro meristem culture.

*Time to initiate roots*.—About seven to eight days at soil temperatures about 15° C. and ambient temperatures about 20° C.

*Time to produce a rooted young plants*.—About four weeks at soil temperatures about 15° C. and ambient temperatures about 20° C.

*Root description*.—Medium in thickness; fleshy; color, close to 162C.

*Rooting habit*.—Freely branching; medium density.

Plant description:

*Plant and growth habit*.—Herbaceous perennial; tall and upright to somewhat outwardly spreading and mounded plant habit; dense and bushy appearance; vigorous growth habit; moderate growth rate.

*Plant height*.—About 50 cm to 60 cm.

*Plant width*.—About 40 cm to 50 cm.

*Lateral branches (peduncles)*.—Length: About 30 cm to 35 cm. Diameter: About 4 mm to 6 mm. Internode length: About 5 cm to 10 cm. Angle: Upright to somewhat outwardly spreading. Strength: Strong. Texture: Rough, pubescent. Color: Close to 144A; spots, close to 187A.

Leaf description:

*Arrangement*.—Alternate or opposite, simple; sessile.

*Length*.—About 8 cm to 25 cm.

*Width*.—About 2 cm to 5 cm.

*Shape*.—Oblanceolate.

*Apex*.—Acute to acuminate.

*Base*.—Attenuate.

*Margin*.—Dentate; undulate.

*Texture, upper and lower surfaces*.—Pubescent; rough.

*Venation pattern*.—Pinnate.

*Color*.—Developing and fully expanded leaves, upper surface: Close to 137A; venation, close to 145B. Developing and fully expanded leaves, lower surface: Close to 137C; venation, close to 145B.

Inflorescence description:

*Type and arrangement*.—Single-type inflorescence form with lanceolate to oblanceolate-shaped ray florets and tubular disc florets; inflorescences borne on terminal and axillary peduncles above and beyond the foliar plane on strong peduncles; ray and disc florets arranged acropetally on a capitulum.

*Fragrance*.—None detected.

*Flowering season*.—Plants begin flowering about ten weeks after planting; long flowering period, plants flower continuously from mid-July until the end of October in The Netherlands.

*Inflorescence longevity*.—Good postproduction longevity with inflorescences lasting about eight to ten weeks on the plant; inflorescences persistent.

*Quantity of inflorescences*.—Freely flowering habit, typically more than 50 inflorescences developing per plant during the flowering season.

*Inflorescence buds*.—Height: About 1 cm to 2 cm. Diameter: About 1 cm to 2 cm. Shape: Round. Color: Close to 145A.

*Inflorescences*.—Diameter: Large, about 10 cm to 15 cm. Depth (height): About 3 cm to 4 cm. Diameter of disc: About 2 cm to 3.5 cm. Receptacle height: About 5 mm to 8 mm. Receptacle diameter: About 7 mm to 10 mm. Receptacle color: Close to 144A.

*Ray florets*.—Number of ray florets per inflorescence: About 12 to 20 arranged in a single whorl. Length: About 6 cm to 7 cm. Width: About 1.5 cm to 2 cm. Shape: Lanceolate to oblanceolate. Apex: Emarginate. Base: Attenuate. Margin: Entire. Texture, upper surface: Smooth, glabrous. Texture, lower surface: Rough, glabrous. Color: When opening, upper surface: Distally, close to 17A; proximally, close to N167A to N167B; venation, similar to lamina colors. When opening, lower surface: Close to 151D; venation, close to 145B. Fully opened, upper surface: Distally, close to 17A; proximally, close to 175B and N172B; at the base, close to 200A; venation, similar to lamina colors; color does not change with development. Fully opened, lower surface: Close to 152D; venation, close to 145B.

*Transitional florets*.—Number of ray florets per inflorescence: About 12 to 20 arranged in a single whorl. Length: Small, about 1 cm to 2 cm. Width: About 5 mm. Shape: Lanceolate. Apex: Emarginate. Base: Attenuate. Margin: Entire. Texture, upper and lower surfaces: Smooth, glabrous. Color: When opening, upper and lower surfaces: Close to 145A. Fully opened, upper and lower surfaces: Close to 200A and 175B.

*Disc florets*.—Arrangement: Numerous disc florets massed at center of receptacle. Length: About 1 cm to 2 cm. Width: About 1 mm to 2 mm. Shape: Tubular, elongated. Apex: Obtuse. Color, when opening and fully opened: Close to N187A.

*Phyllaries*.—Number of phyllaries per inflorescence: About 20 to 30 in about two whorls. Length: About 1.5 cm to 3 cm. Width: About 3 mm to 7 mm. Shape: Lanceolate. Apex: Acute to obtuse. Base: Fused. Margin: Entire; slightly undulate. Texture, upper and lower surfaces: Rough, pubescent. Color, upper surface: Close to 146A. Color, lower surface: Close to 146B.

*Reproductive organs*.—Androecium (present on ray and disc florets): Quantity per floret: Numerous. Filament length: About 1 mm to 2 mm. Filament color: Close to N187A. Anther shape: Round. Anther length: About 1 mm to 2 mm. Anther color: Close to N187A. Pollen amount: Abundant. Pollen color: Close to 12A. Gynoecium (present only on disc florets): Pistil length: About 2 mm to 3 mm. Stigma shape: Two-parted. Stigma color: Close to N187A. Style length: About 1 mm to 2 mm. Style color: Close to N187A.

*Seeds and fruits*.—To date, seed and fruit production has not been observed on plants of the new *Rudbeckia*.

Pathogen & pest resistance: To date, plants of the new *Rudbeckia* have not been observed to be resistant to pathogens and pests common to *Rudbeckia* plants.

Garden performance: Plants of the new *Rudbeckia* have been observed to have good garden performance and to tolerate wind, rain and temperatures from about −20° C. to about 40° C.

It is claimed:

1. A new and distinct *Rudbeckia* plant named 'ET RDB 603' as illustrated and described.

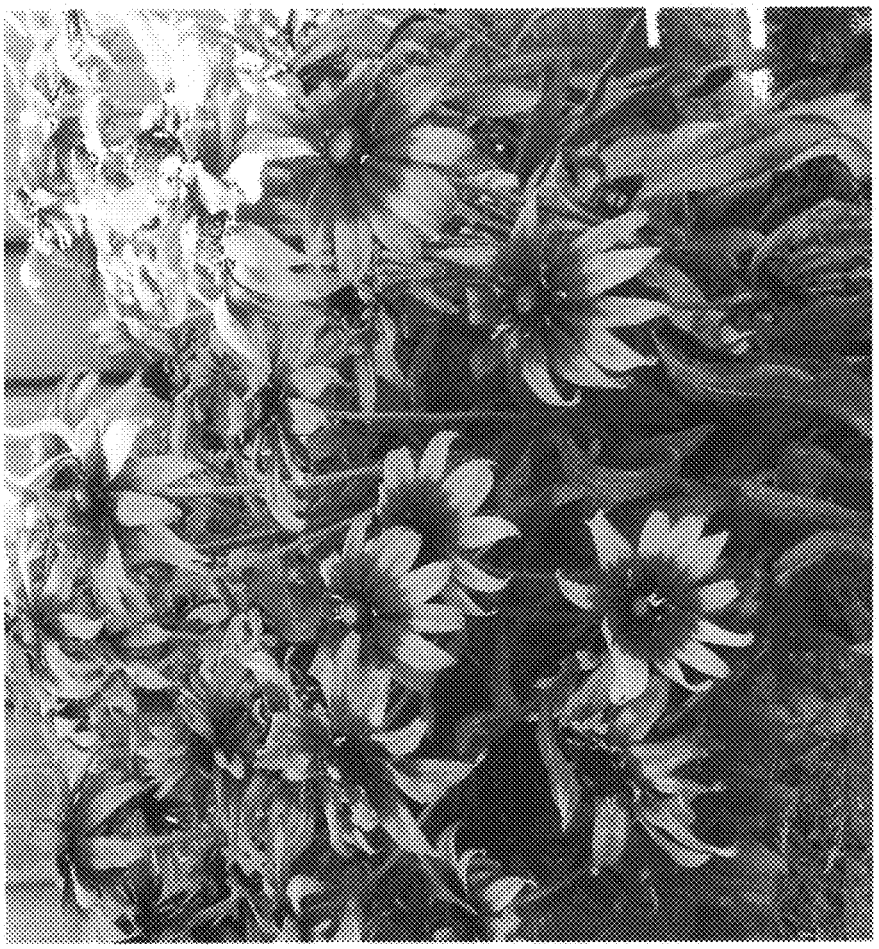

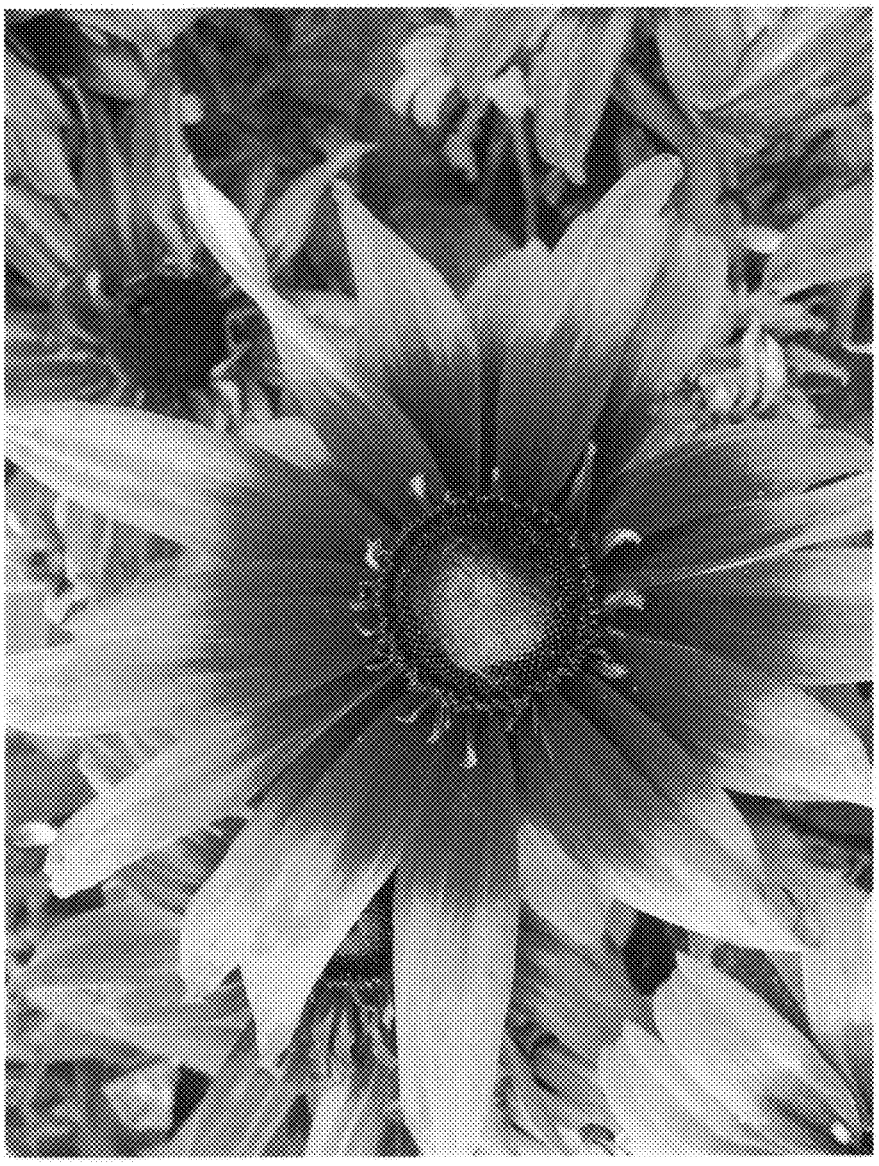

* * * * *